(12) United States Patent
Elefanty et al.

(10) Patent No.: US 10,894,944 B2
(45) Date of Patent: Jan. 19, 2021

(54) CELL CULTURE MEDIA

(75) Inventors: Andrew George Elefanty, Surrey Hills (AU); Edouard Guy Stanley, Ascot Vale (AU); Elizabeth Siewsun Ng, Surrey Hills (AU)

(73) Assignee: Monash University, Victoria (AU)

( * ) Notice: Subject to any disclaimer, the term of this patent is extended or adjusted under 35 U.S.C. 154(b) by 244 days.

(21) Appl. No.: 12/756,785

(22) Filed: Apr. 8, 2010

(65) Prior Publication Data

US 2010/0317104 A1 Dec. 16, 2010

Related U.S. Application Data

(60) Provisional application No. 61/168,424, filed on Apr. 10, 2009.

(51) Int. Cl.
*C12N 5/0735* (2010.01)

(52) U.S. Cl.
CPC ........ *C12N 5/0606* (2013.01); *C12N 2500/25* (2013.01); *C12N 2500/36* (2013.01); *C12N 2500/60* (2013.01); *C12N 2500/92* (2013.01)

(58) Field of Classification Search
CPC .............................. A61K 35/12; C12N 5/0606
See application file for complete search history.

(56) References Cited

U.S. PATENT DOCUMENTS

| | | | |
|---|---|---|---|
| 5,811,297 A * | 9/1998 | Gopal | C12N 5/0639 435/320.1 |
| 6,627,440 B1 * | 9/2003 | Murgita | 435/404 |
| 6,762,053 B2 * | 7/2004 | Gardner et al. | 435/407 |
| 7,455,983 B2 * | 11/2008 | Xu et al. | 435/7.21 |
| 7,989,205 B2 * | 8/2011 | Moscatello | 435/407 |
| 8,137,971 B2 * | 3/2012 | Poole | 435/383 |
| 2002/0129394 A1 * | 9/2002 | Aso | C12N 15/873 800/15 |
| 2007/0077649 A1 * | 4/2007 | Sammak et al. | 435/325 |

FOREIGN PATENT DOCUMENTS

WO WO1997033978 * 9/1997
WO WO2007026353 * 3/2007

OTHER PUBLICATIONS

Gadue et al (PNAS, 7; 103(45): 16806-11, 2006).*
Costa et al (Nat Methods, 2: 259-260, 2005).*
Yang et al (J Nutr Biochem, 20(7):537-43, 2009 Epub Sep. 11, 2008).*
Synthecho sigma pdf; //www.sigmaaldrich.com/life-science/cell-culture/synthechol-ns0.html (p. 1-6).*
Hay et al (PNAS, 105( 34): 12301-12306, 2008).*
Damude et al (Physiologia Plantarum 132: 1-10, 2008).*
Han et al (J. Nutr. 132: 904-910, 2002).*

* cited by examiner

*Primary Examiner* — Anoop K Singh
*Assistant Examiner* — Magdalene K Sgagias
(74) *Attorney, Agent, or Firm* — Bozicevic, Field & Francis LLP; Karl Bozicevic

(57) ABSTRACT

A serum-free media composition for maintenance or directed differentiation of human embryonic stem cells (HESCs) toward particular cell lineages is disclosed. The media comprises one or more cell nutrient media, a recombinant human albumin or equivalent thereof and optionally at least one agent involved in HESC differentiation. The media composition is substantially free of any human or animal derived products.

28 Claims, 12 Drawing Sheets a  Envy d4 EBs b  d3 spin EBs c

CELL CULTURE MEDIA

FIELD OF THE INVENTION

The present invention relates to improved serum-free cell culture media composition. In particular the present invention relates to an improved serum-free cell culture media composition for maintenance or differentiation of human embryonic stem cells (HESCs) wherein the media composition comprises a recombinant human albumin, and is substantially free of any human and animal derived products.

BACKGROUND OF THE INVENTION

The isolation and in vitro propagation of human embryonic stem cell lines (HESCs) has created possibilities for the study of early stages of human development, the generation of in vitro models for human diseases, testing of pharmaceuticals and other therapeutic products, as well as the production of transplantable cells for tissue repair and regeneration.

A necessary requirement for the progression of both these research and therapeutic agenda is the ability to reproducibly and robustly direct the differentiation of HESCs towards designated lineages. The composition of the media in which the cells are cultured and differentiated is arguably one of the most important factors that contributes to the success or failure of HESC differentiation in vitro. The observed batch-to-batch variation in the purity and bioactivity of individual media components negatively impacts on the reproducibility of results, and introduces unknown components that also affect the differentiation process. Specifically, the inventors observed that the response of differentiating HESC (and mouse embryonic stem cells) to exogenously added cytokines and growth factors is critically dependent on the composition of the base media in which the cells differentiate.

The composition of culture medium will be a critical factor influencing the efficiency and safety of differentiated HESCs as a source of cell types with potential therapeutic applications. The inclusion of variable and poorly defined serum-derived components in cell culture media introduces unknown elements that are likely to affect the efficiency and reproducibility of differentiation outcomes in response to exogenously added growth factors. Furthermore, animal or human components potentially expose cells to infectious agents, posing an unacceptable risk for cells prepared for clinical use. Indeed, the recent discovery that some batches of Matrigel™ (BD Biosciences), a commonly used extracellular matrix derived from the EHS murine sarcoma cell line, harbour lactate dehydrogenase elevating virus (LDEV), underscores the risk of adventitious exposure to pathogens inherent with media containing animal derived products.

Serum free media for the maintenance and differentiation of HESCs have recently been reported (Lu et al. (2006) *Proc Natl Acad Sci USA* 103, 5688-5693; Ludwig et al. (2006) *Nat Biotechnol* 24, 185-187; Yao et al. (2006) *Proc Natl Acad Sci USA* 103, 6907-6912). However, the TeSR1 medium described by Ludwig et al. contains human serum albumin that is not fully defined, and the HESCs were maintained on a mixture of human matrix components. The N2 B27-CDM used by Yao et al. for both maintenance and differentiation of HESCs contained bovine serum albumin, the cells were cultured on Matrigel™ (BD Biosciences) and included B27 supplement, an additive which contains animal products. The serum free medium denoted HESCO (Lu et al. (2006) *Proc Natl Acad Sci USA* 103, 5688-5693) included human albumin and fibronectin and embryoid bodies were generated in medium containing 10% fetal calf serum. Indeed, examination of recently published manuscripts describing protocols for the directed differentiation of HESCs towards multiple therapeutically relevant lineages such as hematopoietic mesoderm (Kennedy et al. (2007) *Blood* 109, 2679-2687; Lu et al. (2007) *Nat Methods* 4, 501-509; Olivier et al. (2006) *Exp Hematol* 34, 1635-1642), muscle, bone and fat (Barberi et al. (2007) *Nat Med* 13, 642-648), pancreatic endoderm (D'Amour et al. (2006) *Nat Biotechnol* 24, 1392-1401; Jiang et al. (2007) *Cell Res* 17, 333-344) and oligodendrocytes (Keirstead et al. (2005) *J Neurosci* 25, 4694-4705), revealed that all differentiation methods required the inclusion of animal or human components in the medium. Therefore for embryonic stem cell derived products to be clinically useful cell therapies, there is a need to develop stem cell maintenance and differentiation media that is free of animal or human derived products.

SUMMARY OF THE INVENTION

In a first aspect of the present invention there is provided a serum-free media composition for maintenance or directed differentiation of human embryonic stem cells (HESCs) towards desired cell lineages, wherein the media composition comprises:
(i) one or more nutrient media;
(ii) a recombinant human albumin or equivalent thereof; and optionally
(iii) at least one agent involved with HESC differentiation
and wherein the media composition is substantially free of any animal and human derived products.

In a second aspect of the present invention there is provided a method for cultivating and differentiating human embryonic stem cells (HESCs), the method comprising contacting a population of HESCs with a serum-free media composition according to the first aspect of the invention, and cultivating the HESCs under serum-free conditions suitable to facilitate expansion and differentiation of HESCs, wherein the media composition is substantially free of any animal and human derived products.

In a third aspect of the present invention there is provided a population of expanded and differentiated human embryonic stem cells (HESCs) obtained by the method according to the second aspect of the invention.

In a fourth aspect of the present invention there is provided a kit comprising a serum-free media composition according to the first aspect of the invention, wherein the at least one agent involved with cell differentiation is packaged separately within the kit.

BRIEF DESCRIPTION OF THE FIGURES

As shown in FIG. 3h, the inclusion of FGF2 in the growth factor cocktail did not influence the generation of cardiomyocytes.

DEFINITIONS

Figure 1:
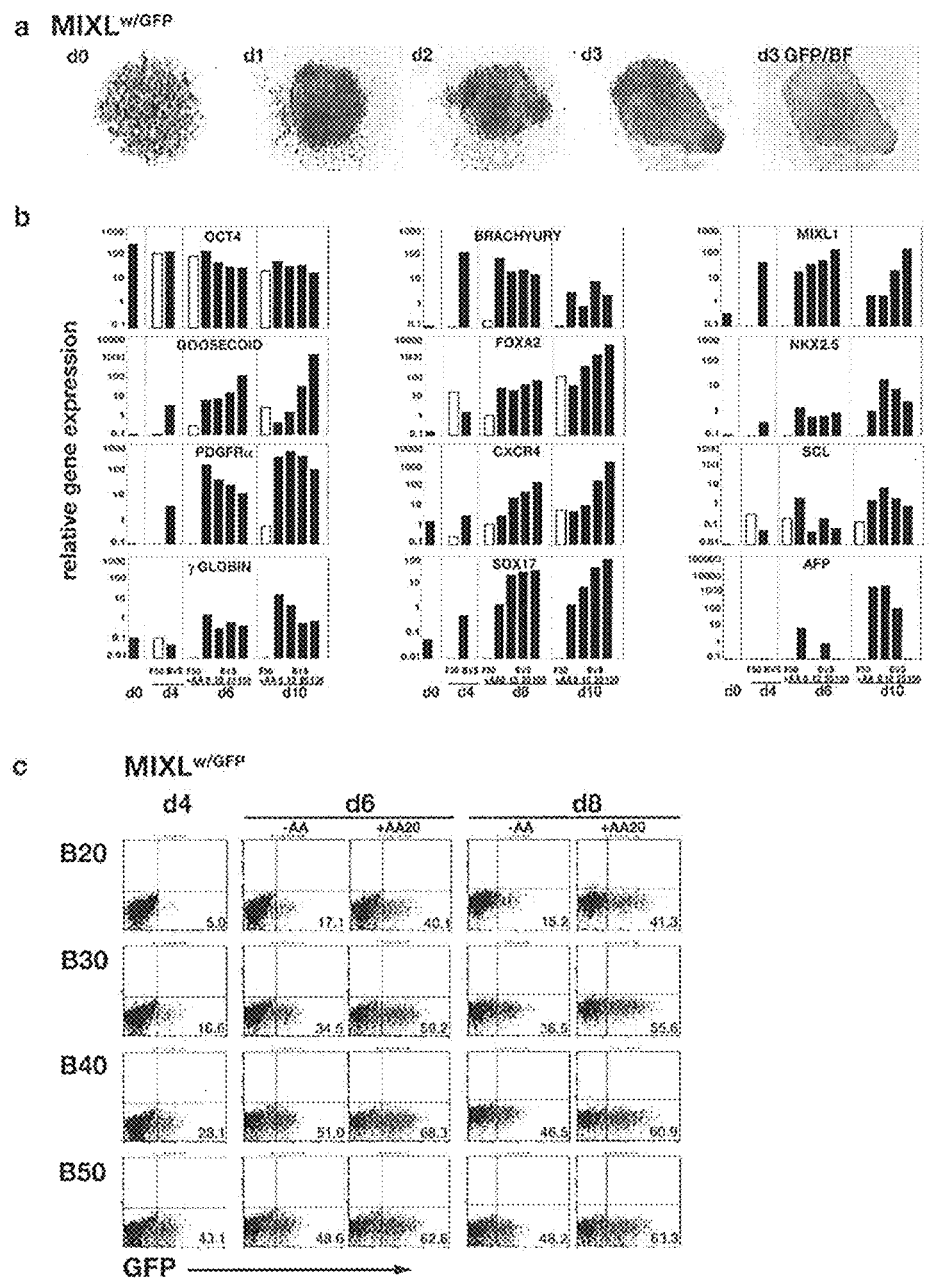
FIG. 1 shows differentiation of $Mixl1^{GFP/w}$ and Envy HESC in APEL medium. APEL media supports BMP4 and Activin induced mesendodermal differentiation of HESCs (a) Time course analysis of $Mixl1^{GFP/w}$ spin EBs differentiated in APEL medium supplemented with BMP4 40 ng/ml, VEGF 30 ng/ml and SCF 40 ng/ml form a single EB per well. By differentiation d3, GFP, which reports expression of the mesendoderm marker, MIXL1, could be clearly observed by fluorescence microscopy. BF, brightfield. (b) RT-PCR analysis of HESCs differentiated in APEL media demonstrated that expression of lineage specific marker genes was modulated by the combination of growth factor supplements. Envy EBs were differentiated in APEL media supplemented with 50 ng/ml FGF2 (F50) or 40 ng/ml BMP4, 20 ng/ml VEGF and 40 ng/ml SCF (BVS). 10-100 ng/ml of Activin (AA) was added to d4 BVS initiated cultures as indicated. EBs were harvested for analysis by Taqman real time PCR at days 0, 4, 6, 10. (c) Flow cytometric analysis of differentiating Mixl1$^{GFP/w}$ cells demonstrated that GFP expression was dependent on the concentration of BMP4 and was augmented by a combination of BMP4 and Activin A.

The term "APEL" as used herein means a serum-free media composition which is substantially free of any animal and human derived products, the components of which are as defined in Table 1.

The term "derived" as used in the context of "animal or human derived products" means products isolated from a human or animal source, and excludes any recombinant products including recombinant proteins.

The term "AEL" as used herein means APEL media without polyvinylalcohol (PVA) included.

The term "BPEL" as used herein means APEL media in which the recombinant human albumin is replaced with bovine serum albumin.

The term "HPEL" as used herein means APEL media in which the recombinant human albumin is replaced with human serum albumin.

The term "IMDM" as used herein means to Iscove's Modified Dulbecco's Medium (Invitrogen; Table 5) a nutrient media comprising various inorganic salts, amino acids, vitamins and other protein components.

The term "F12" or "Ham's F12" as used herein refers to F12 nutrient mixture (Invitrogen; Table 5) with or without L-glutamine.

The term "rHA" as used herein means recombinant human albumin. The term "Albucult" as used herein is a trade mark of Delta Biotechnology for rHA.

The term "equivalent thereof" in the context of "recombinant human albumin or equivalent thereof" means an embryonic form of human albumin.

The term "polymeric alcohol" as used herein means a polymeric compound comprising one or more alcohol groups, and includes, but is not limited to polyvinyl alcohol (PVA) and polyethylene glycol (PEG).

The term "polymeric lactam" as used herein means a polymeric compound comprising one or more lactam groups, and includes, but is not limited to, polyvinylpyrrolidone (PVP).

The term "essential fatty acid" as used herein means an essential fatty acid that cannot be synthesised by the human body and includes, but is not limited to, linoleic and linolenic acids.

The terms "linoleic acid" and "linolenic acid" as used herein means plant derived forms of linoleic acid and linolenic acid, respectively.

The term "Synthechol" as used herein means synthetic cholesterol 3β-Hydroxy-5-cholestene.

The term "α-MTG" as used herein means α-monothioglycerol.

The term "rhITS-X" as used herein means a mixture of recombinant human insulin, recombinant human transferrin, ethanolamine and sodium selenite as defined in Table 3.

The term "PFHMII" as used herein means protein free hybridoma media.

The term "Glutamax 1" as used herein means the synthetic dipeptide L-alanyl-L-glutamine. Glutamax 1 is the trade mark of Invitrogen for L-alanyl-L-glutamine (Table 6).

The term "cultivate" and "cultivating" as used herein means cells that are maintained, cultured or grown in an artificial, in vitro environment.

The term "serum-free media" as used herein means a media which contains no serum.

The terms "maintenance" and "maintain", in the context of maintenance of HSCs, as used herein means culturing human embryonic stem cells in an undifferentiated state.

DETAILED DESCRIPTION OF THE INVENTION

In a first aspect of the present invention there is a provided a serum-free media composition for maintenance or differentiation of human embryonic stem cells (HESCs) towards desired cell lineages, wherein the media composition comprises:
(i) one or more nutrient media;
(ii) a recombinant human albumin or equivalent thereof, and optionally
(iii) at least one agent involved with HESC differentiation
    and wherein the media composition is substantially free of any animal and human derived products.

In an embodiment according to the first aspect of the present invention, the nutrient media is selected from the group consisting of IMDM, F12 and protein free hybridoma medium as defined above.

In an embodiment according to the first aspect of the present invention the at least one agent involved with HESC differentiation is selected from growth factors and cytokines. Examples of growth factors include, but are not limited to, fibroblast growth factors (FGF) including FGF-2, transforming growth factor-β (TFG-β) including Activin A, bone morphogenetic proteins (BMP) including BMP-4, vascular endothelial growth factor (VEGF) and stem cell factor (SCF). Examples of cytokines include, but are not limited to, Wnt proteins including Wnt3a and Wnt5a, BMPs including BMP-2, BMP-4, BMP-5, BMP-7, platelet derived growth factor (PDGF) and insulin-like growth factor (IFG) including IGF-2.

In an embodiment according to the first aspect of the present invention, the serum-free media composition further comprises one or more components selected from the group consisting of a polymeric alcohol or lactam, one or more essential fatty acids, one or more sterols, recombinant human insulin, one or more anti-oxidants, one or more synthetic forms of a naturally occurring amino acid, one or more antibiotics, transferrin or transferrin substitutes, one or more trace elements, and optionally, at least one agent involved with cell differentiation.

In a further embodiment of the present invention the recombinant human albumin is recombinant alpha-fetoprotein or a variant thereof (Kubota et al. (2002) *J. Biol. Chemistry* 277: 27629-27635).

In a further embodiment of the present invention the polymeric alcohol or lactam is selected from the group consisting of polyvinyl alcohol (PVA), polyethyleneglycol (PEG) and polyvinylpyrrolidone (PVP).

In another embodiment of the present invention, the one or more essential fatty acids is selected from the group consisting of linoleic acid and linolenic acid.

In yet another embodiment of the present invention, the one or more sterols is synthetic cholesterol.

In yet another embodiment of the present invention, the naturally occurring amino acid is selected from the group consisting of L-glutamine, L-asparagine, L-threonine, L-serine, L-cysteine and L-tyrosine, glycine, L-alanine, L-aspartic acid, L-glutamic acid, L-phenylalanine, L-histidine, L-isoleucine, L-lysine, L-leucine, L-methionine, L-proline, L-threonine, L-tryptophan and L-valine. Preferably the naturally occurring amino acid is L-glutamine.

In yet another embodiment of the present invention the anti-oxidant is selected from the group consisting of ascorbic acid, a mercaptol alcohol, glutathione, thiamine or dithiothreitol (DTT). The anti-oxidant may be ascorbic acid 2 phosphate or mercaptol alcohol, and the mercaptol alcohol may be α-monothioglycerol (also referred to as β-mercaptoethanol).

In yet another embodiment of the present invention the antibiotic is selected from the group consisting of penicillin and streptomycin.

In yet a further embodiment of the present invention, the transferrin substitute is an iron chelate selected from the group consisting of ferric acid chelate and ferrous sulfate chelate.

In yet a further embodiment of the present invention, the trace element is selected from the group consisting of $Ag^+$, $Al^{3+}$, $Ba^{2+}$, $Cd^{2+}$, $Co^{2+}$, $Cr^{3+}$, $Ge^{4+}$, $Se^{4+}$, $Br^-$, $I^-$, $Mn^{2+}$, $F^-$, $Si^{4+}$, $V^{5+}$, $Mo^{6+}$, $Ni^{2+}$, $Rb^+$, $Sn^{2+}$ and $Zr^{4+}$. It is preferred that the trace element is $Se^{4+}$.

In another embodiment of the present invention the serum-free media composition comprises at least one nutrient media, recombinant human albumin or equivalent thereof, a polymeric alcohol or lactam, recombinant human insulin, and at least one synthetic form of a naturally occurring amino acid.

In a further embodiment of the present invention the serum-free media composition comprises one or more nutrient media, recombinant human albumin, polyvinylalcohol, linoleic acid, linolenic acid, synthetic cholesterol, α-monothioglycerol, recombinant human insulin, recombinant human transferrin, sodium selenite, ethanolamine, a protein free hybridoma medium, ascorbic acid 2 phosphate, a synthetic dipeptide L-alanyl-L-glutamine, and an antibiotic.

The serum-free media composition according to the present invention is substantially free of human and animal derived products. Accordingly, in an embodiment of the present invention the protein component of the serum-free media composition is comprised of recombinant proteins.

The recombinant proteins may be produced using routine methods known to those skilled in the art, an includes recombinant production techniques involving eukaryotic or prokaryotic host cells including yeast, plant cells, fungi, *Escherichia coli* or insect cells, but not including cells derived from vertebrates.

The media composition of the present invention may also be used to cultivate HESCs undergoing differentiation, as well as differentiated HESCs.

The media of the present invention may also be used to maintain and differentiate HESCs from multiple different lineages. The different HESC lineages include, but are not limited to, HES3, H1 and MEL1.

In yet another embodiment, the media composition is formulated as a concentrated media composition.

In a second aspect of the present invention there is provided a method for expanding and differentiating HESCs, the method comprising contacting a population of HESCs with a serum-free media composition according to the first aspect of the invention, and cultivating the HESCs under serum-free conditions suitable to facilitate expansion and differentiation of HESCs, wherein the media composition is substantially free of animal and human derived products.

In a third aspect of the present invention there is provided a population of expanded and differentiated HESCs obtained by the method according to the second aspect of the invention.

The present invention also contemplates a kit comprising a serum-free media composition of the invention. Accordingly, in a fourth aspect of the present invention there is provided a kit comprising a serum-free media composition according to the first aspect of the invention, wherein the at least one agent involved with cell differentiation is packaged separately within the kit. The at least one agent involved with cell differentiation may be selected from the group consisting of FGF including FGF2, TFG-β including Activin A, BMP including BMP-2, BMP-4, BMP-5 and BMP-7, VEGF, SCF, Wnt proteins including Wnt3a and Wnt5a, PDGF and IGF including IGF-2.

In an embodiment of the present invention the kit comprises a serum-free media composition and at least one agent involved with cell differentiation, wherein the at least one agent involved with cell differentiation directs differentiation of HESCs towards ectoderm, mesoderm or endoderm.

In order that the nature of the present invention may be more clearly understood, preferred forms thereof will now be described with reference to the following non-limiting definitions and examples.

EXAMPLE 1

Methods

Preparation of Media

The components for APEL medium are listed in Table 1. The composition of stock solutions, commercial sources for reagents and catalogue numbers are given in Tables 2-6. Stock solutions of recombinant human insulin-transferrin-selenium-ethanolamine supplement (rhITS-Eth) and polyvinylalcohol (PVA) were pre-prepared and stored at 4° C. The components for the preparation of the rhITS-Eth supplement are given in the Tables 3 and 4. The 5% or 10% PVA stock solution was generally prepared by dissolving the solid in $dH_2O$ at 4° C. for several days. To facilitate initial solubilisation, the PVA solution may be incubated at 37° C. overnight or heated to 85-90° C. for 1-2 minutes and then pre-filtered through a 0.45 μm filter unit (INTERPATH PES filter, Nylon membrane) to reduce viscosity. Most of the differentiations were performed using 10% PVA stock.
Preparation of APEL A PVA-lipid mixture was prepared by diluting the required volume of PVA stock in ~20% of the final volume of IMDM and Ham's F12 in a 50 ml tube. Linolenic and linoleic acids and SyntheChol™ were added and the tube contents mixed by vigorous shaking. This step was required to prevent the PVA forming discrete droplets within the medium. The remaining media components (IMDM, Ham's F12, Albucult, ☐MTG, ITS-Eth, PFHMII, ascorbic acid, GlutamaxI, penicillin and streptomycin) were added directly to the upper chamber of a 0.22 μm SteriCup filtration unit to which the PVA-lipid mixture was then added prior to filtration. If necessary, a glass 0.45 μm filter disc (MILLIPORE) can be placed on the 0.22 μm filter surface of the upper chamber of the SteriCup unit to faciltate filtration. The filtration step was essential for the combination of the medium components as well as for ensuring sterility. APEL medium prepared without cytokines could be stored at 4° C. for at least 10 days.
Culture, Maintenance and Differentiation of HES Cells The human ESC lines HES3 (Reubinoff et al (2000) *Nat Biotechnol* 18, 399-404), the GFP-expressing HES3 derivative, Envy (Costa et al. (2005) *Nat Methods* 2, 259-260), the MIXL1-targeted HES3 line MIXL1$^{GFP/w}$, the WiCell line H1 (Thomson et al. (1998) *Science* 282, 1145-1147) and the MEL1 and 2 lines (ASCC/Stem Cell Sciences Inc) were maintained on irradiated (30 Gy) mouse embryo fibroblasts (PMEFs) in HESC medium (DMEM/F12 (Invitrogen) containing 20% Serum Replacer (KOSR, Invitrogen), and 10 ng/ml recombinant human FGF2 (rhFGF2, Peprotech)). HESC lines were routinely maintained by mechanical passaging to ensure karyotype stability and stock cultures were expanded enzymatically for 10 to 25 passages for use in differentiation experiments as recently described in detail (Costa et al. (2007) *Nat Protoc* 2, 792-796). All lines retained a normal karyotype on repeated testing and expressed high levels of the stem cell markers GCTM-2, E-cadherin, Tra-1-60 and Oct-4 by flow cytometry.

HESC were differentiated as spin EBs as previously described (Ng et al. (2005) *Blood* 106, 1601-1603). Subconfluent HESCs were enzymatically dissociated and replated onto fresh PMEFs seeded at low density (1.0×10$^4$ cells/cm$^2$) on the day prior to differentiation. The following day, cells were dissociated into a single cell suspension using either animal-product free TrypLE Select™ (Invitrogen, GIBCO) or a recombinant trypsin, TrypZean (SIGMA). TrypZean was neutralized with Soybean Trypsin Inhibitor (SIGMA). Dissociated cells were washed in phosphate buffered saline (PBS) and resuspended in APEL medium. Recombinant human growth factors were used at the following concentrations unless otherwise indicated: FGF2 50 ng/ml (PeproTech), BMP4 40 ng/ml (R&D Systems), VEGF 20 ng/ml (PeproTech), SCF 40 ng/ml (PeproTech). EB formation was induced by seeding the desired number of cells in 100 μl of APEL medium plus growth factors into each well of 96-well round bottom, low attachment plates (Nunc plate bases, Nunc plate lids, or Costar 96 well polystyrene assay plates, Corning Inc) using a multichannel pipette. The plates were then centrifuged at 1500 rpm for 3 mins at 4° C. to aggregate the cells. In some experiments, at d4 of differentiation, a proportion of the EBs were supplemented with Activin A (R&D Systems) at 10, 20 or 100 ng/ml. In some experiments, the EBs were transferred after 10-12 days to tissue culture treated plates (BD Falcon) in fresh medium supplemented with the recombinant human cytokines, VEGF 20-50 ng/ml, SCF 40 ng/ml, interleukin-3 (IL-3) 30 ng/ml, interleukin-6 (IL-6) 30 ng/ml, Thrombopoietin (Tpo) 30 ng/ml and Erythropoietin (Epo) 3 U/ml (all from PeproTech) for hematopoietic or cardiac differentiation or 10$^{-6}$M retinoic acid for neural induction.
BPEL and HPEL Media The Albumin source was the only component that differed between APEL and BPEL or HPEL media. BPEL medium contained BSA instead of Albucult and, as untreated BSA frequently proved to be cytotoxic, the 10% stock solution of BSA in dH$_2$O was de-ionized through three changes of Resin Beads (AG501-XB(D) 20-50 mesh) (BioRad) prior to use. Several variations of BPEL were used where the ratio of BSA to PVA concentrations were reduced from 10:1 (0.5% BSA and 0.05% PVA) to 1:1 (0.25% BSA and 0.25% PVA), reducing the cost of the medium without affecting the outcome of the differentiation process or the cell viability.

HPEL media was prepared using a commercially available 10% human serum albumin stock at a 10:1 ratio to PVA (0.5% HAS and 0.05% PVA).
Colony Forming Assays Colony forming assays were set up as triplicates cultures in 24-well low-attachment plates (Nunc). Aliquots of 0.5 ml of serum-free MethoCult™ (Stem Cell Technologies) per well containing 10,000 to 25,000 input cells from dissociated EBs were supplemented with the following recombinant human growth factors: VEGF 50 ng/ml, SCF 100 ng/ml, IL-3 30 ng/ml, IL-6 30 ng/ml, Tpo 30 ng/ml and Epo 3 U/ml (all from PeproTech). Plates were incubated at 37° C. in a humidified atmosphere in a 5% CO$_2$ incubator and scored for colony formation between d10 and d14.
Cytocentrifuge Preparations Single colonies were harvested at various stages of maturity and spun onto glass slides using a Shandon Cytocentrifuge 4, stained with May-Grünwald-Giemsa (Sigma) and examined using a Zeiss Axiovert 200 microscope. Images were obtained with a Zeiss Axiocam and processed with Axiovision software.
Antibody Staining and Flow Cytometry EBs at different stages of differentiation were dissociated into single cells using TrypLE Select™ and resuspended in a block solution (PBS supplemented with 2% fetal calf serum, 1% goat serum and 1% rabbit serum) and incubated with appropriate isotype control antibodies (BD Biosciences) or the following monoclonal antibodies: anti-E-cadherin (HECD1, Zymed), anti-PDGFRα (CD140a, BD Biosciences), anti-CXCR4-Phycoerythrin conjugate (CD184a, BD Biosciences), anti-CD34-Phycoerythrin conjugate (clone 8G12, BD Biosciences) and anti-TroponinT (MAB1874, R&D systems). Cells were incubated in diluted primary antibody for 30 min on ice, rinsed twice in FACS wash (PBS with 2% FCS) and incubated as required with APC-conjugated secondary antibody for 20 min on ice. The cells were rinsed twice in FACS wash prior to analysis. Propidium iodide staining was used to exclude dead cells. Cells were analysed on a FACSCalibur (Becton Dickinson) using CellQuest software (Becton Dickinson).
Gene Expression Analysis Total RNA from undifferentiated and differentiated HESC was extracted using RNeasy reagents (Quiagen) according to the manufacturer's instructions. DNase treated samples were reverse transcribed with random hexamer priming using the Superscript III kit (Invitrogen Corporation). Real time PCR was performed using Taqman gene expression probes and Taqman reagents purchased from Applied Bioscience and the 7500 Fast Real-time PCR system absolute thermal cycler and software (Applied Bioscience, Ca). The comparative cycle threshold (Ct) method was used to analyze data, with gene expression levels compared to a reference gene, GAPDH. GAPDH was chosen for the reference gene because recent experiments in our laboratory have demonstrated that it is more robust and sensitive measure of amplifiable cDNA in differentiating HESCs than other reference genes such as UBIQUITIN C or HPRT. The Ct for expression was calculated for each gene and for the GAPDH reference gene (REF). Since gene expression is inversely proportional to the Ct, the expression for a given target gene relative to REF may be given by the formula:

$$GeneExpression \propto \frac{1}{2^{Ct(Gene-REF)}}$$

The calculated value was generally multiplied by a factor of 1000 for the purposes of presentation.

EXAMPLE 2

Results

Figure 5:
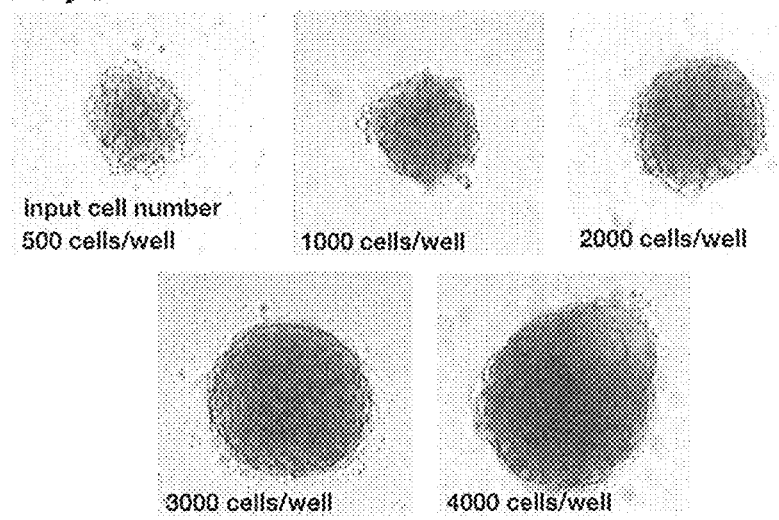
FIG. 5 shows HESC differentiated in APEL medium form spin EBs with a size proportional to the input cell number. (a) Brightfield images of d4 spin EBs formed from Envy cells showing that EB size is proportional to the d0 input cell number per well. (b) Day 3 spin EBs formed in APEL from H1, MEL1, MEL2 and hES3 cells display similar morphology. (c) Additional gene expression data generated with differentiating Envy cells from the experiment shown in FIG. 1b.
Figure 5:
Figure 5:
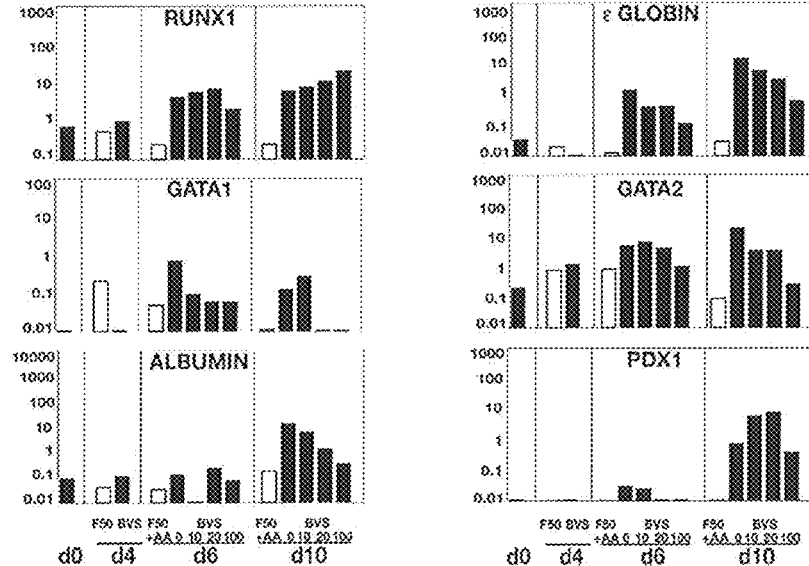

APEL medium is based on the Chemically Defined Medium (CDM) described in Johansson et al. (1995) *Mol Cell Biol* 15, 141-151. We have previously shown that a modified version of CDM containing Protein-free Hybridoma Medium (an animal-free product from Invitrogen), ascorbic acid 2 phosphate and Glutamax (Invitrogen), supported robust and reproducible hematopoietic differentiation of HESCs as spin spin embryoid bodies (spin EBs; Ng et al. (2005) *Blood* 106, 1601-1603). In APEL, purified bovine serum albumin, transferrin and insulin were replaced with recombinant human counterparts and the Chemically Defined Lipids (Invitrogen) (which include cholesterol derived from sheep's wool) were replaced with synthetic cholesterol and linoleic and linolenic acids, essential fatty acids, sourced from plants (Tables 1-5). The inclusion of polyvinylalcohol (PVA), a water-soluble synthetic polymer, in APEL was a key component that ensured the formation of a single EB in each well (FIG. 5). All components used in this medium are commercially available (Table 6).

TABLE 1

Composition of APEL media

IMDM
Ham's F12
recombinant human albumin (Albucult ®)
Polyvinylalcohol (PVA)
Linoleic acid
Linolenic acid
synthetic cholesterol (SyntheChol ™)
αMTG
rhuman Insulin-Transferrin-Selenium-Ethanolamine
Protein Free Hybridoma Medium II
Ascorbic acid 2 phosphate
GlutaMax I
Penicillin/Streptomycin

TABLE 2

Composition of APEL media

| Medium component (final concentration) | Stock solution | Volume per 200 ml |
|---|---|---|
| 1 x IMDM | 1 X | 86.2 |
| 1 x F12 | 1 X | 86.2 |
| rHuman Albumin (5 mg/ml)* | 100 mg/ml (10%) | 10 ml |
| Polyvinylalcohol (PVA) (0.05% w/v) | 5% or 10% | 1-2 ml |
| Linoleic acid (100 ng/ml) (see SuppTable 4) | 100x 100 X | 20 µl |
| Linolenic acid (100 ng/ml) (see SuppTable 4) | 100x 100 X | 20 µl |
| SyntheChol (2.2 µg/ml) (see SuppTable 4) | 72x 100 X | 27.8 µl |
| αMTG (3.9 µl/100 ml; ~350-450 µM) | 13 µl in 1 ml IMDM | 600 µl |
| rhITS-Eth (see SuppTables 2 &3) | 100 X | 2 ml |
| PFHMII (5%) | 1 X | 10 ml |
| Ascorbic acid 2 phosphate (50 µg/ml) | 5 mg/ml | 2 ml |
| GlutaMax I (2 mM) | 200 mM (100 X) | 2 ml |
| Penicillin/Streptomycin (100U Pen G/ 100 µg Streptomycin sulfate) | 200 X | 1 ml |

TABLE 3

Generation of rhITS-Eth component stock solutions

| Medium component | stock solution |
|---|---|
| Sodium selenite | 70 mg/100 mls in PBS (0.7 mg/ml) |
| recombinant human insulin | 5 mg/ml in PBS |
| holo transferrin | 20 mg/ml |
| Ethanolamine ≥ 98% (16.6M) | 100 mg/ml (500x) in PBS |

TABLE 4

Generation of rhITS-Eth 100 X working solution

| Component stock solution | volume per 10 ml |
|---|---|
| Sodium selenite 70 mg/100 mls | 10 µl |
| rhInsulin 5 mg/ml | 2 mls |
| rhTransferrin 20 mg/ml | 275 µl (36.5 × dil) |
| ethanolamine 100 mg/ml | 20 µl |
| PBS | 7.9 mls |

TABLE 5

Lipid solutions

| Medium component | stock solution |
|---|---|
| linoleic acid (99% pure) | 10 µl (10 mg) in 10 mls EtOH = 1 mg/ml; 10,000 X |
| linolenic acid (99% pure) | 10 µl (10 mg) in 10 mls EtOH = 1 mg/ml; 10,000 X |
| SyntheChol (Sigma #C1231) | 16 mg/ml in EtOH; 7,200 X |

TABLE 6

Components and Suppliers

| Medium component | Supplier |
|---|---|
| IMDM (-phenol red) | Invitrogen |
| F12 nutrient mixture With Glutamax I | Invitrogen |
| Albucult (rHA) | Novozymes Delta Ltd |
| Human serum albumin | Sage Turnbull |
| PVA | Sigma |
| Linoleic acid | Sigma |

TABLE 6-continued

| Medium component | Supplier |
| --- | --- |
| Linolenic acid | Sigma |
| SyntheChol | Sigma |
| aMTG | Sigma |
| PFHMII | Invitrogen |
| Ascorbic acid 2 phosphate | Sigma |
| Glutamax I (L-Alanyl-L-glutamine) | Invitrogen |
| Sodium selenite | Sigma |
| Recombinant human insulin | Sigma |
| Holo transferrin | Novozymes Delta Ltd |
| Ethanolamine ≥98% (16.6M) | Sigma |
| Penicllin/Streptomycin | Invitrogen |

Inclusion of PVA in APEL Increases the Propensity of Spin EB

Inclusion of PVA in APEL increases the propensity of spin EB's differentiation cultures to form single rather than multiple EBs in individual wells in the 96-well format used. The formation of a single EB in each well is desirable because it increases the uniformity, synchrony and reproducibility of differentiation. Furthermore, the size of the EB influences differentiation outcome (even in the presence of Activin or BMP4, EBs containing large cell numbers (e.g. initiated with >4000 cells/EB) favour neural differentiation whilst EBS formed from lower cell numbers (e.g. initiated with 2000-3000 cells/EB) favour mesendoderm).

Figure 6:
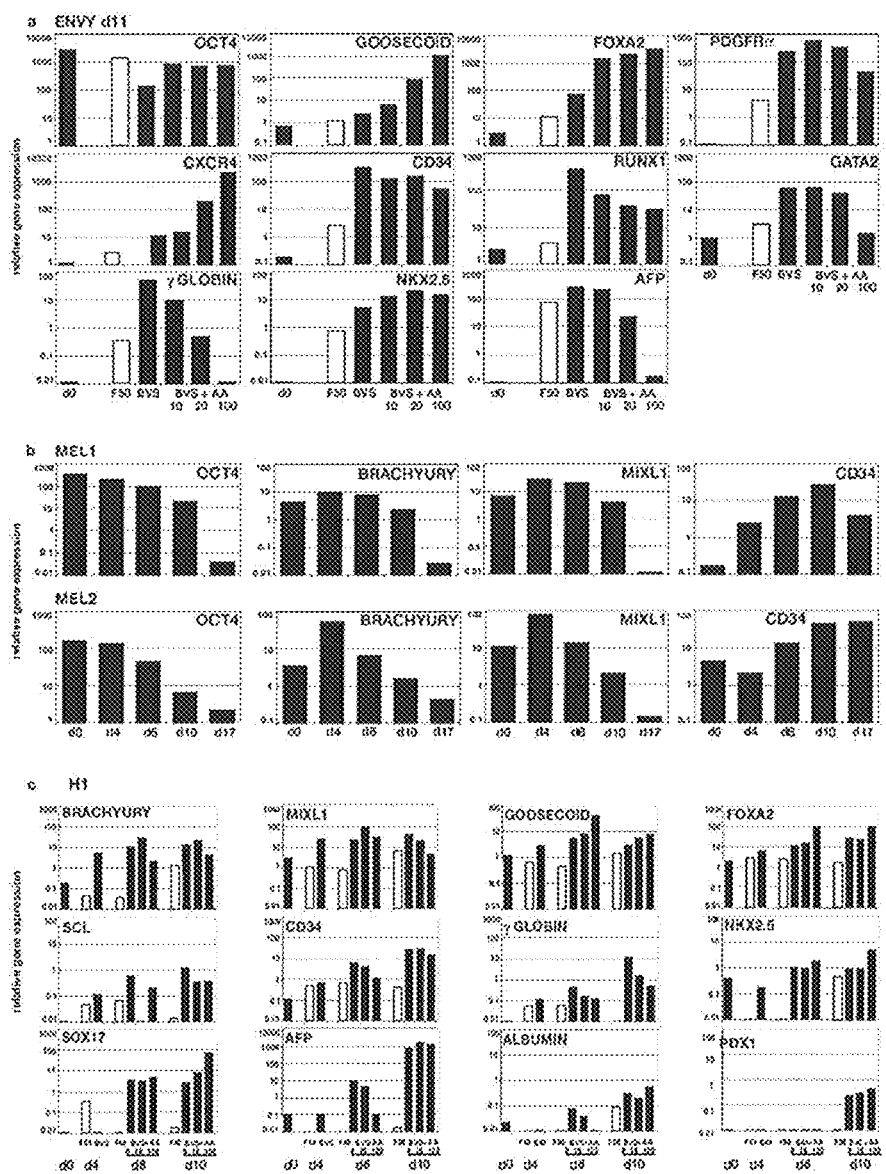
FIG. 6 shows gene expression of differentiating Envy, MEL1 and H1 spin EBs in APEL medium. Gene expression data generated from (a) an independent experiment using Envy cells differentiated in FGF2, BVS and BVS/Activin analysed at d11, (b) MEL1 and MEL2 cells differentiated in APEL with BVS at the indicated time-points and (c) H1 cells, differentiated in FGF2, BVS and BVS/Activin analysed at the indicated time-points.
Figure 9:
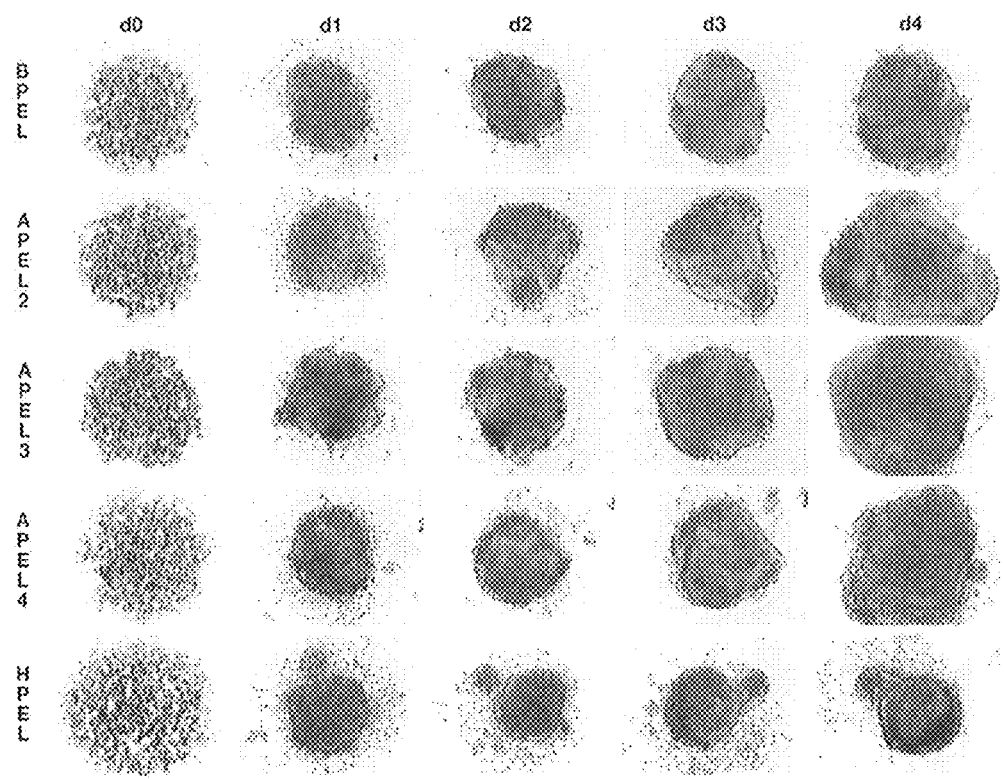
FIG. 9 shows HESC form spin EBs of uniform morphology in BPEL, APEL and HPEL media. Brightfield images of differentiating MIXL1$^{GFP/w}$ spin EBs formed in BPEL, three independent batches of APEL (APEL2, 3 and 4) and HPEL media. Images of the same representative EB formed in each media were captured daily for 4 days, demonstrating the increased size of the EBs generated in APEL media and the increased cell death seen in HPEL medium. (Original magnification ×50 for d0 and ×100 for days 1, 2, 3 and 4).

APEL Medium Supports BMP4 and Activin A Induced Mesendodermal Differentiation of HESCs Spin EB differentiation cultures initiated in APEL medium supplemented with bone morphogenetic protein 4, vascular endothelial growth factor and stem cell factor (BVS) consistently formed a single EB in each well by d1 with an EB size proportional to the input cell number (FIGS. 1a, 5 and 9). Analysis of Envy spin EBs by real time PCR showed expression of the stem cell gene OCT4 was down-regulated with differentiation in all growth factor combinations (FIG. 1b). By d4 of differentiation, the primitive streak genes BRACHYURY, MIXL1 and GOOSECOID were expressed in APEL medium supplemented with BVS (APEL/BVS) (FIG. 1b). Titration of Activin into APEL/BVS medium increased and prolonged the expression levels of MIXL1, GOOSECOID and FOXA2 in d6 EBs in a dose dependant manner, consistent with previous reports showing that Activin induces genes associated with the anterior primitive streak (Gadue et al. (2006) Proc Natl Acad Sci USA 103, 16806-16811). The BMP4 and Activin responsiveness of these genes was observed in additional independent experiments with Envy, MEL1, MEL2 and H1 ESC lines (FIGS. 5 and 6). Expression of primitive streak genes was not detected in cultures differentiated in the absence of added growth factors (data not shown) or in the FGF2 supplemented cultures (FIGS. 1b and 6), demonstrating a requirement for exogenously supplied BMP4 or Activin signalling to initiate the processes of mesendodermal differentiation from hESCs (Ng et al. (2005) Blood 106, 1601-1603; Pick et al. (2007) DOI: 10.1634/stemcells.2006-0713. Stem Cells).

The capacity for APEL medium to support BMP4 and Activin mediated mesendoderm induction was corroborated by flow cytometric analysis of differentiating $MIXL1^{GFP/w}$ HESCs, a targeted HESC line in which GFP is a reporter for MIXL1 expression and thus marks primitive streak stage cells (FIG. 1a). $MIXL1^{GFP/w}$ cells were differentiated in APEL supplemented with 20-50 ng/ml BMP4, VEGF and SCF. At d4, Activin was added to a subset of these cultures. Flow cytometric analysis showed a BMP4 dose-dependent increase in the frequency of $GFP^+$ cells, which peaked at d6 in response to 40 ng/ml BMP4 (FIG. 1c). Supplementation with Activin increased the percentage of $GFP^+$ cells and the intensity of GFP fluorescence, consistent with the enhanced MIXL1 expression noted in response to Activin in Envy cells (FIG. 1b).

Supplementation of APEL Media with Combinations of BMP4 and Activin Modulates the Frequency of PDGFR $\alpha^+$ and $CXCR4^+$ Cells in Differentiating HESCs In the developing mammalian embryo, platelet-derived growth factor receptor (PDGFRα) is initially expressed on cells in the primitive streak and nascent mesoderm, and is later predominantly found on paraxial mesoderm, neural crest derivatives and glia (Kataoka et al. (1997) Dev Growth Differ 39, 729-740; Xu et al. (2005) Dev Dyn 232, 75-84). In mouse ESCs, PDGFRα expression has been used to monitor differentiation to paraxial mesoderm and mesenchymal tissues (Nishikawa et al. (1998) Development 125, 1747-1757; Tada et al. (2005) Development 132, 4363-4374; Takebe et al. (2006) Dev Biol 293, 25-37), and we have observed that PDGFRα expression is a sensitive indicator of primitive streak and nascent mesoderm in differentiating human ESC. The chemokine receptor CXCR4 is expressed in migrating endoderm and mesoderm early in development, although it displays a more complex expression pattern on subsets of neural, endodermal and mesodermal cells post gastrulation (McGrath et al. (1999) Dev Biol 213, 442-456). Therefore, we examined the expression of these two genes in HESCs differentiated in APEL media, anticipating that their expression patterns might change in response to varying combinations of BMP4 and Activin, factors which have been implicated in mesoderm and endoderm development respectively (Gadue et al. (2006) Proc Natl Acad Sci USA 103, 16806-16811; Tada et al. (2005) Development 132, 4363-4374; D'Amour, et al. (2005) Nat Biotechnol 23, 1534-1541; Yasunaga et al. (2005) Nat Biotechnol 23, 1542-1550). PDGFRα expression in differentiating HESCs was BMP4-dependent for the first 10 days and was reduced in response to increasing concentrations of Activin (FIG. 1b). Conversely, CXCR4 levels increased in response to Activin, consistent with recent studies (D'Amour, et al. (2005) Nat Biotechnol 23, 1534-1541). These data are also consistent with the hypothesis that Activin patterns cells to an anterior primitive streak-like population that is fated to give rise to dorsal mesoderm and definitive endoderm (Gadue et al. (2006) Proc Natl Acad Sci USA 103, 16806-16811; Tada et al. (2005) Development 132, 4363-4374; D'Amour, et al. (2005) Nat Biotechnol 23, 1534-1541; Yasunaga et al. (2005) Nat Biotechnol 23, 1542-1550). These expression data were confirmed in an independent experiment shown in FIG. 6a.

Figure 2:
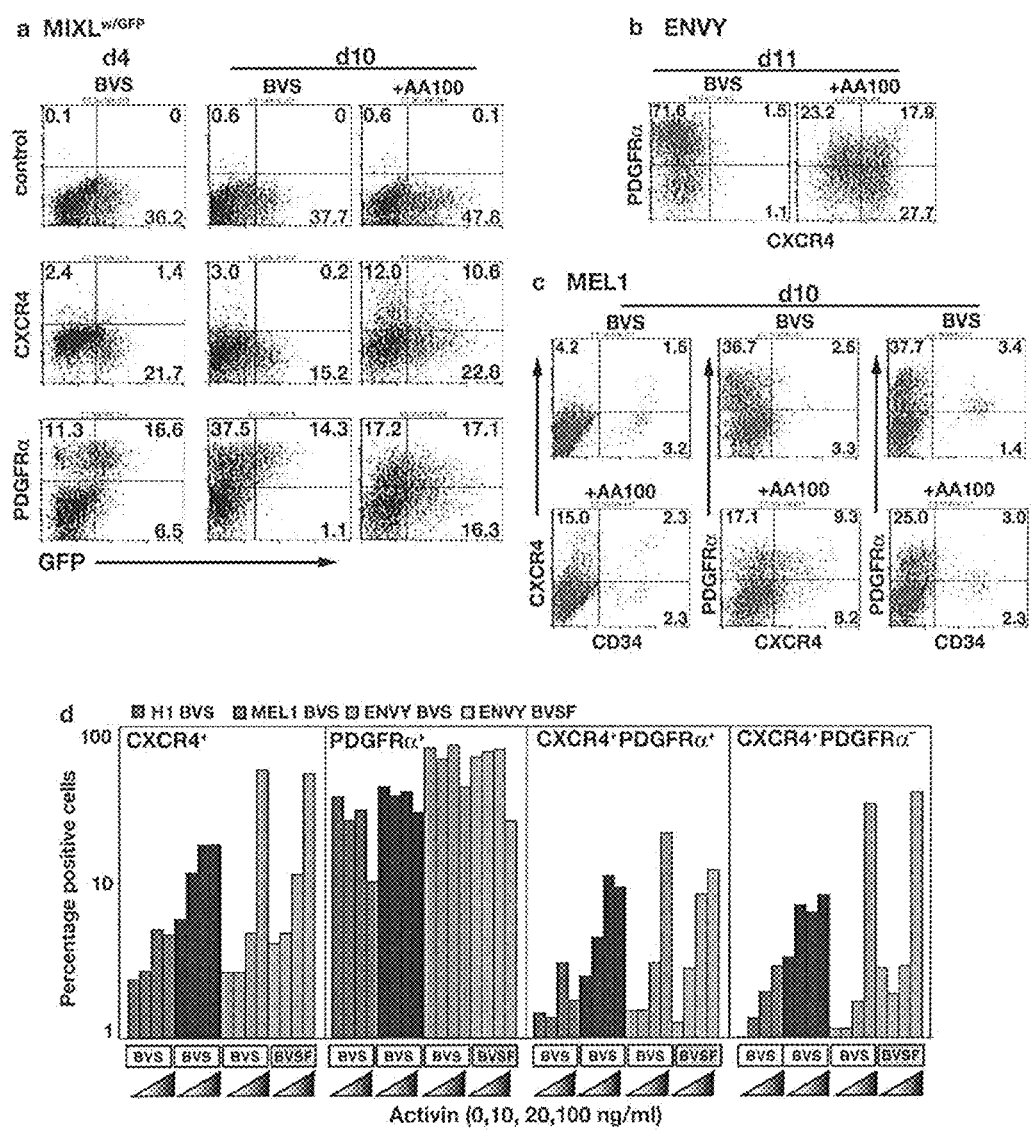
FIG. 2 shows supplementation of APEL media with combinations of BMP4 and Activin modulates the frequency of PDGFRα$^+$ and CXCR4$^+$ cells in differentiating HESCs. (a-c) Flow cytometric analysis of (a) Mixl1$^{GFP/w}$ (b) Envy and (c) MEL1 HESCs differentiated in APEL supplemented with BVS demonstrated that addition of Activin (AA) 100 ng/ml at d4 decreased the frequency of PDGFR α$^+$ cells and increased the proportion of CXCR4$^+$ cells. In (c) co-expression of the haematopoietic mesoderm marker CD34 with CXCR4$^+$ and PDGFR α$^+$ cells indicates that early CXCR4 expression marks mesoderm. (d) Graphical representation of data from flow cytometric analyses at d10 of H1, MEL1 and Envy cells differentiated in APEL media with BVS or BVSF supplemented with 0-100 ng/ml Activin A at d4. Addition of Activin increased in CXCR4$^+$PDGFR α$^+$ presumptive mesodermal cells and CXCR4$^+$PDGFR α$^+$ presumptive endodermal cells in a dose dependent manner and decreased the percentage of PDGFR α$^+$ cells at the highest concentrations of Activin.

Examination of the levels of PDGFRα and CXCR4 protein expression on the surface of HESCs differentiated in APEL/BVS with or without Activin confirmed the changes in expression observed by PCR analysis (FIG. 2). In $MIXL1^{GFP/w}$ cells treated with Activin, there was a reduction in the proportion of cells expressing PDGFRα and an increase in the percentage of $CXCR4^+$ cells, accompanied by the expected increase in the frequency $GFP^+$ cells (FIG. 2a). This relationship between PDGFRα and CXCR4 expression in response to increasing concentrations of Activin A was consistently observed during the differentiation of Envy, MEL1 and H1 HESC lines (FIGS. 2b-d). The results of four experiments, shown graphically in FIG. 2d, demonstrate an increase in the percentage of CXCR4$^+$ cells as increasing amounts of Activin were titrated into the APEL differentiation medium. Conversely, the total percentage of PDGFRα$^+$ mesodermal cells decreased in response to the highest concentrations of Activin.

Figure 3:
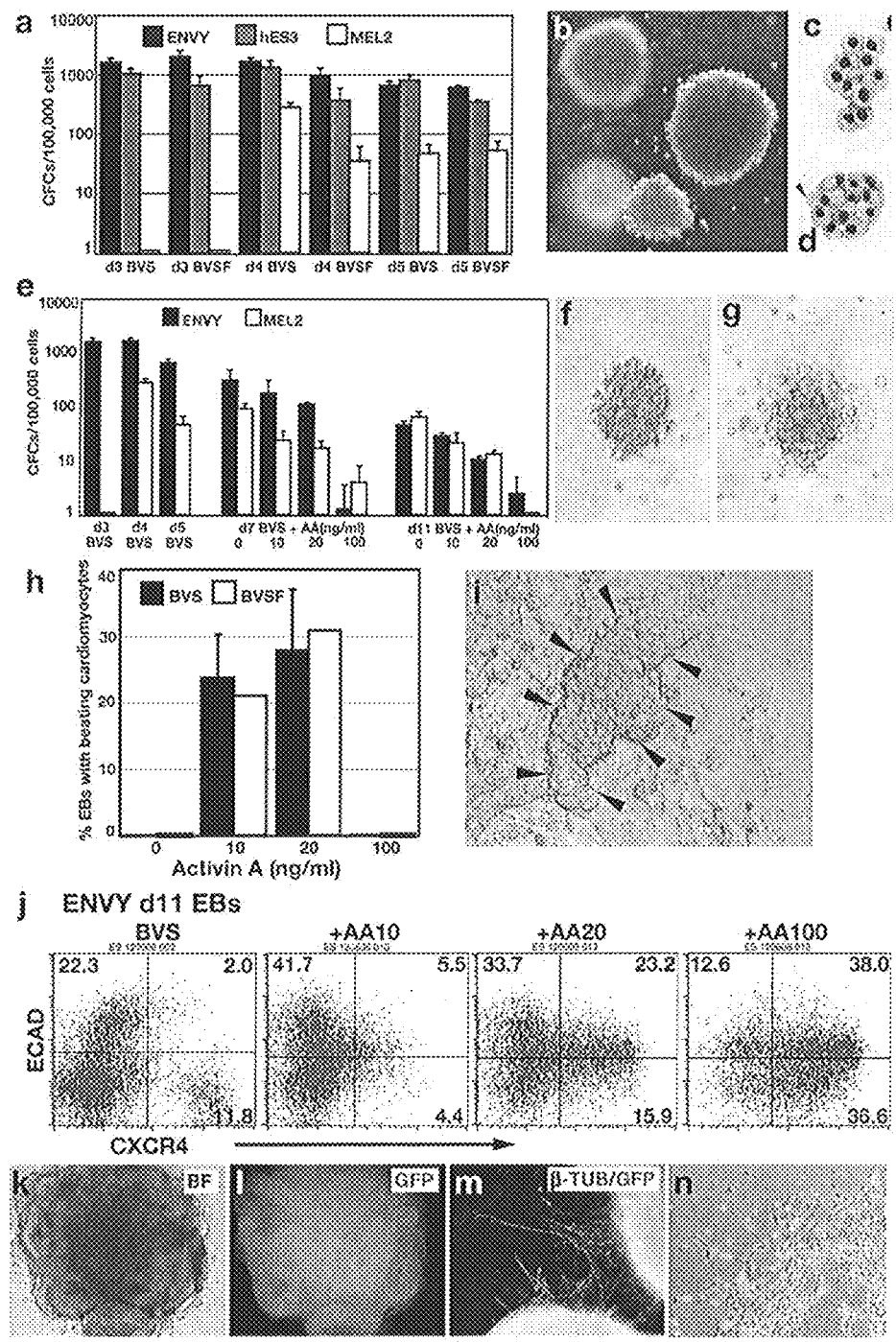
FIG. 3 shows multiple HESCs lines differentiated in APEL media with appropriate growth factors can be induced to form mesodermal, endodermal and ectodermal precursors. (a) Frequency of hematopoietic blast colony forming cells (CFCs) from Envy, hES3 and MEL2 cells differentiated in BVS or BVSF for 3 to 5 days. The frequency of blast forming cells was unaffected by the inclusion of FGF2 in the differentiation medium. (mean±sd of triplicate wells, data sourced from 3 experiments) (b) Images of d24 Mixl1$^{GFP/w}$ blast colonies established in methylcellulose on d4 of differentiation (original magnification ×100). Cytocentrifuge preparations of single colonies (c, d) at d24 of culture demonstrate the presence of primitive erythroid cells with occasional enucleated red cells (d, arrow). (e) Frequency of CFCs in methylcellulose in differentiating Envy and MEL2 cells. Increasing concentrations of Activin were added at d4 to cultures initiated in BVS. Colony assays in methylcellulose were set up at the indicated days and scored 8 to 10 days later. (mean±sd of triplicate wells, data sourced from 2 experiments). Images of (f) erythroid and (g) myeloid colonies from d7 BVS cultures after 13 d in methylcellulose (original magnification ×200) (h) Frequency of spontaneously beating (i) masses of cardiomyocytes (arrowheads, original magnification ×200) in Envy EBs treated with 0-100 ng/ml Activin at d4 and scored d15 to d20 (BVS mean±sem for 5 experiments; BVSF, data represent mean from 2 experiments) showing that cardiomyocyte differentiation occurs in a narrow range of Activin concentrations. (j) Flow cytometric analysis of Envy cells differentiated in APEL and BVS supplemented with 10, 20 or 100 ng/ml Activin A shows a dose dependant increase in E-cadherin$^+$CXCR4$^+$ endoderm precursor cells at d11. (k-n) Neural rosettes in Envy cells differentiated for 10 days in FGF2 50 ng/ml and plated on extracellular matrix for 3 d (k, brightfield and l, epifluorescence). (m) Further culture in APEL medium supplemented with retinoic acid induced an outgrowth of neurites detected with anti-β-tubulin antibody. Similar results were obtained with culture on fibronectin (n).

CXCR4$^+$ cells segregated into PDGFRα$^+$ and PDGFRα$^-$ subpopulations, and whilst their ultimate fate is not known, it would be reasonable to hypothesise that CXCR4$^+$ PDGFRα– may be presumptive endodermal cells and CXCR4$^+$PDGFRα$^+$ cells might represent mesodermal precursors. Consistent with these hypotheses, we observed that a subset of CD34$^+$ mesodermal cells also co-expressed CXCR4 (FIG. 2c) and that differentiated Envy cells co-expressed E-cadherin and CXCR4 in an Activin dependent fashion indicative of the emergence of definitive endoderm (Yasunaga et al. (2005) Nat Biotechnol 23, 1542-1550; FIG. 3j).

Figure 7:
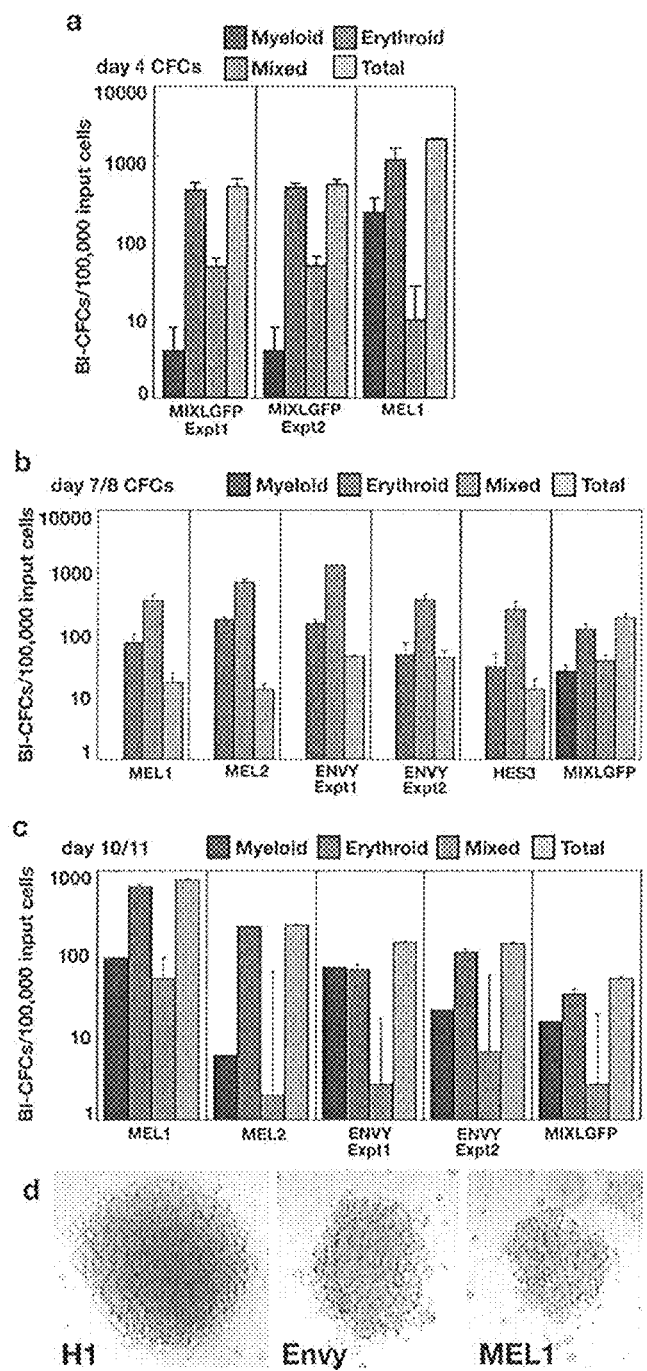
FIG. 7 shows hematopoietic colony forming cells are generated from multiple HESC lines differentiated in APEL medium. Histograms showing the frequency of (a) d4 (b) d7/8 and (c) d10/11 colony forming cells in methylcellulose assays from EBs differentiated in APEL with BVS formed from (a) MIXL1$^{GFP/w}$ and MEL1 cells at d4 (b) MIXL1$^{GFP/w}$, MEL1 and 2, Envy and hES3 cells at d7/8 and (c) Mixl1$^{GFP/w}$, MEL 1 and 2, and Envy cells at d10/11. Data represent mean±sd of triplicate wells, from (a) 3 experiments (b) 6 experiments and (c) 5 experiments. (d) Images of d4 blast colonies generated from H1, Envy and MEL1 cells in methylcellulose after 10 days (original magnification ×200).

APEL Medium Supports the Growth Factor Dependent Differentiation of HESCs into Precursors Representing Mesoderm, Endoderm and Ectoderm Real time PCR analysis demonstrated that HESCs differentiated in APEL/BVS expressed genes representing a range of mesodermal and endodermal cell types (FIGS. 1b, 6 and 7). For example, the growth factor dependent expression of key hematopoietic regulators GATA2, RUNX1 and SCL and the primitive erythroid genes GATA1, ε and γ GLOBIN predicted that APEL/BVS would support hematopoietic differentiation. Similarly, the upregulation of FOXA2, SOX17 and suppression of BMP4-induced Alphafetoprotein (AFP) expression in response to Activin implied APEL medium would also allow the generation of endodermal precursors. Interestingly, expression of the cardiac marker NKX2.5 was maximally induced at intermediate Activin concentrations, suggesting that APEL media would allow the resolution of graded responses to specific factor combinations. Finally, we noted that expression of genes representing the mesodermal and endodermal lineages was greatly reduced in differentiations where APEL media was supplemented with FGF2 alone (APEL/FGF2).

To corroborate this gene expression data, hematopoietic colony forming assays were performed at d3, 4 and 5 of differentiation on EBs formed in APEL/BVS with and without FGF2 (FIG. 3a). Maximal colony frequency was observed at d3-4 of differentiation for Envy, HES3 and MEL2 lines. Inclusion of FGF2 did not significantly influence the outcome, in contrast to recent findings that FGF2 was essential for efficient colony formation under their differentiation conditions (Kennedy et al. (2007) Blood 109, 2679-2687). These early CFCs displayed a morphology similar to the hematopoietic blast colonies cultured from mouse ESC (Choi et al. (1998) Development 125, 725-732; Kennedy et al. (1997) Nature 386, 488-493; Ng et al. (2005) Development 132, 873-884) and more recently from human ESC (Kennedy et al. (2007) Blood 109, 2679-2687; FIGS. 3b and 7). May Grunwald Giemsa stained cytocentrifuge preparations of individual colonies confirmed that most included predominantly nucleated yolk sac type erythrocytes with occasional enucleated red cells (FIGS. 3c, d). Myeloid cells were frequently observed even in colonies without an obvious admixture, indicating that many colonies were multipotential (data not shown). Analysis of CFC at d7-8 and d10-11 demonstrated a progressive decrease in the total frequency of CFCs, and a shift in morphology towards myeloid lineages (FIG. 7). Inclusion of increasing concentrations of Activin at d4, resulted in a dose dependent reduction in the frequency of CFCs at subsequent time points (FIGS. 3e-g).

Figure 8:
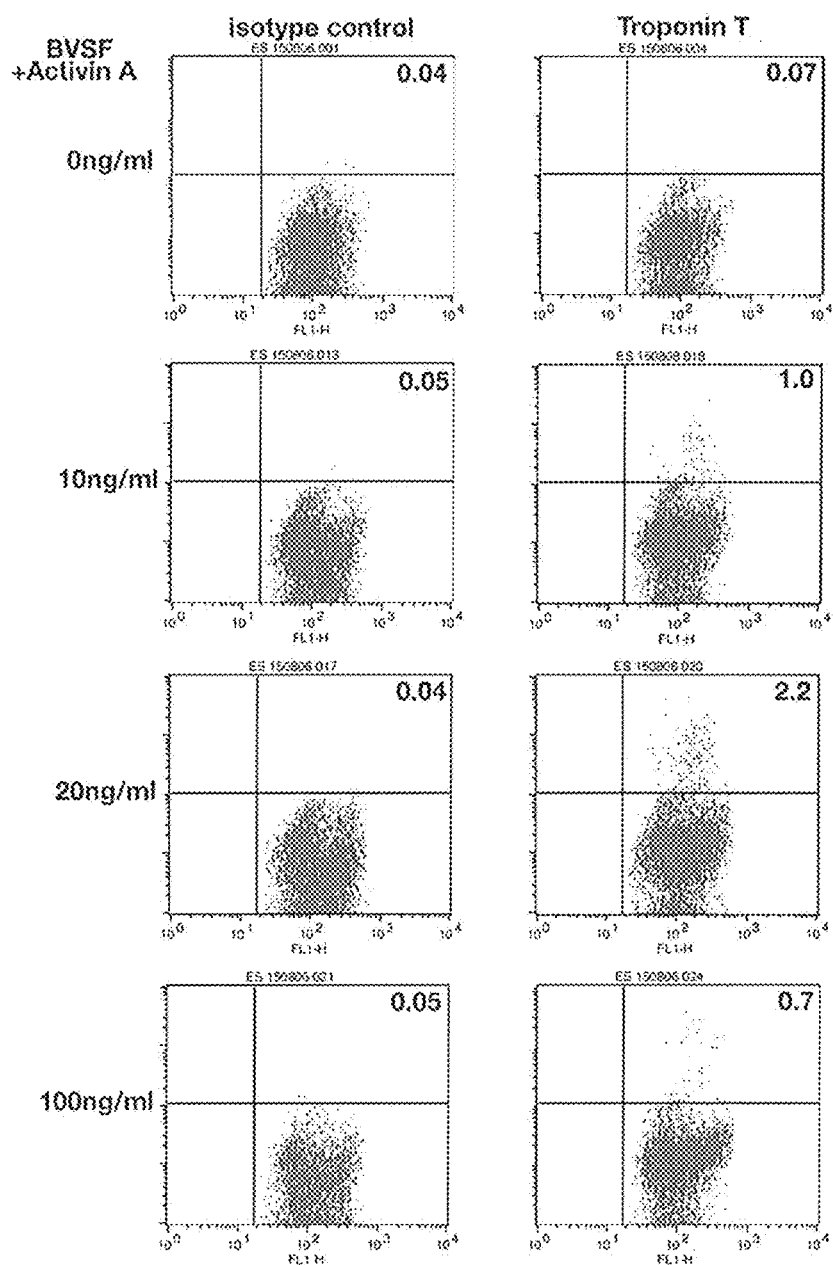
FIG. 8 shows addition of 10-20 ng/ml Activin induces formation of cardiac mesoderm in Envy EBs differentiated in BVSF. Intracellular flow cytometry detecting anti-Troponin T antibody in d28 Envy EBs differentiated in BVSF and the indicated doses of Activin.

The Activin-dependent expression of NKX2.5 shown in FIG. 1b correlated with the appearance of spontaneously contracting clumps of cardiomyocytes in 20-30% of EBs generated in cultures supplemented with 10-20 ng/ml Activin at d15-20 (FIGS. 3h and i). Furthermore, the mature cardiac marker TroponinT was detected by intracellular FACS analysis in EBs treated with either 10 or 20 ng/ml Activin A (FIG. 8).

Gene expression analysis of HESCs differentiated in APEL medium also implied that increasing concentrations of Activin would favour the formation of endodermal progenitors. In this context, it was noteworthy that APEL/BVS medium plus Activin supported the generation of CXCR4$^+$ E-cad$^+$ cells, a population that has been recently identified as endodermal precursors in differentiating mouse ESCs (Yasunaga et al. (2005) Nat Biotechnol 23, 1542-1550). Flow cytometric analysis indicated that the proportion of CXCR4$^+$ E-cad$^+$ cells increased with increasing concentrations of Activin (FIG. 3j).

Quantitative PCR analysis demonstrated that mesendoderm formation was not promoted in APEL media supplemented with FGF2 alone (APEL/FGF2), as evidenced by the failure of these conditions to induce expression of BRACHYURY, MIXL1 or GOOSECOID (FIGS. 1b, 5 and 6) or GFP expression in MIXL1$^{GFP/w}$ EBs (data not shown). Indeed, examination of EBs formed in APEL/FGF2 and transferred to adherent cultures containing extracellular matrix revealed the presence of structures with the morphological appearance of neural rosettes (FIGS. 3k, i). After 6 days treatment with retinoic acid, these EBs generated β-tubulin$^+$ cells with neurites, indicating the pre-existence of neural precursors within the developing APEL/FGF2 EBs (FIGS. 3k-n). Collectively, these results suggest that APEL medium supports the formation of precursors representing mesodermal, endodermal and ectodermal lineages.

Figure 4:
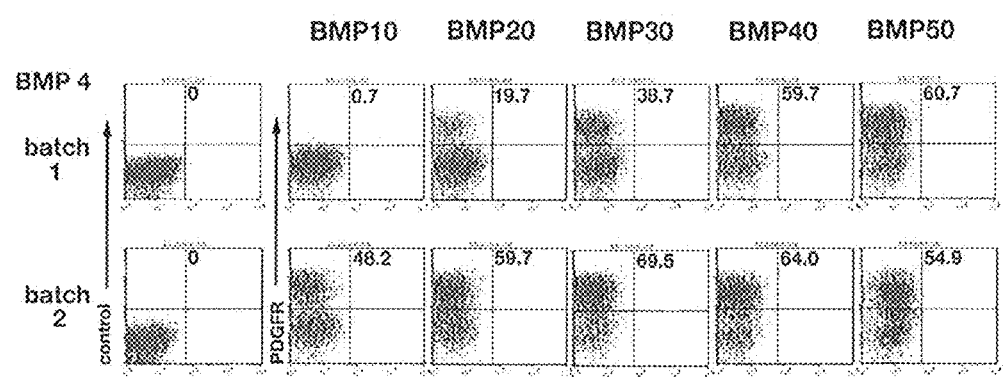
FIG. 4 shows differentiation of HESCs in APEL medium reveals batch variability in the biological activity of BMP4. Flow cytometry of Envy cells differentiated as spin EBs for 7 days in APEL medium supplemented with BVS prepared using two consecutive batches of BMP4 and stained with anti-PDGFRα antibody to reveal mesoderm cells, demonstrating that the potency of BMP4 batch 2 is 2-3 times that of BMP4 batch 1.
Figure 10:
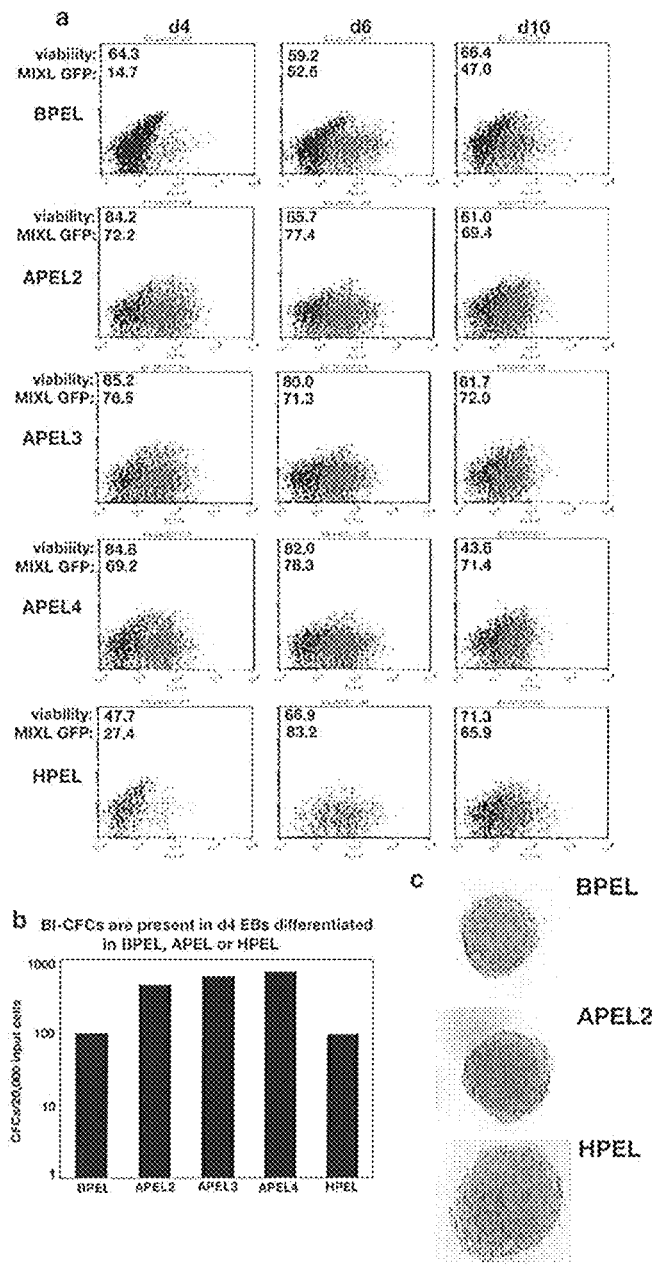
FIG. 10 shows Mixl1$^{GFP/w}$ cells differentiated in APEL show improved early viability and greater induction of GFP expression compared to BPEL and HPEL. (a) Flow cytometry of MIXL1$^{GFP/w}$ cells differentiated for 4, 6 and 10 days in BPEL, three different batches of APEL media, and HPEL showing increased viability in APEL media determined by exclusion of propidium iodide, and a more rapid induction of GFP. (b) Histogram showing increased frequency of colony forming cells from d4 MIXL1$^{GFP/w}$ EBs differentiated in APEL compared with BPEL or HPEL media (mean of triplicate wells, data sourced from 1 experiment). (c) Brightfield images of blast colonies in methylcellulose generated from d4 MIXL1$^{GFP/w}$ EBs differentiated in BPEL, APEL or HPEL media containing BVS showing similar morphological appearance. Colonies were scored and photographed after 8-10 days in methylcellulose. (original magnification ×200).
Figure 11:
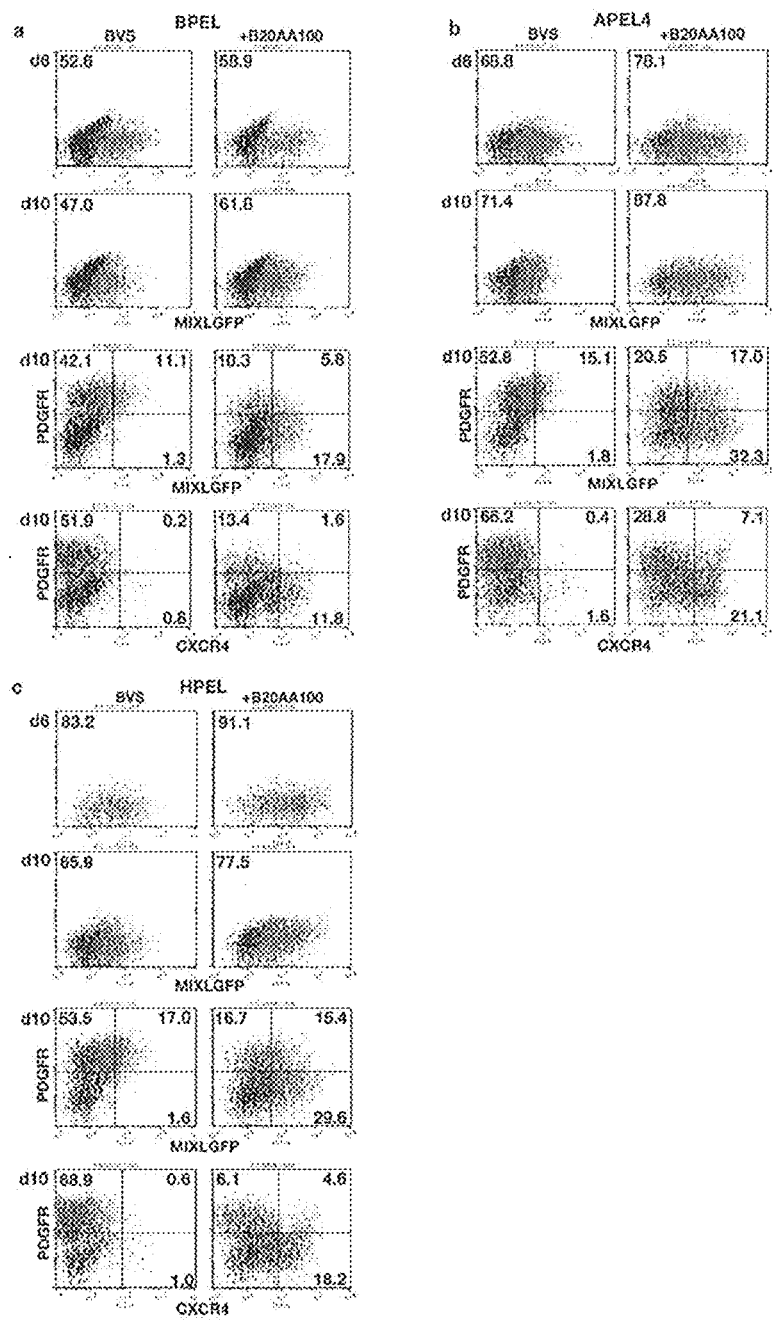
FIG. 11 shows BMP4 and Activin elicit similar inductive and patterning effects on HESC differentiated in BPEL, APEL or HPEL. Flow cytometry at days 6 and 10 of MIXL1$^{GFP/w}$ EBs differentiated in (a) BPEL (b) APEL batch 4 and (c) HPEL with BVS and supplemented with BMP4 20 ng/ml and Activin 100 ng/ml at d4. Similar augmentation of GFP expression from the MIXL1 locus in the presence of Activin was observed with all media formulations. At d10 of differentiation, cells were stained with anti-PDGFRα and anti-CXCR4 antibodies, demonstrating that addition of Activin at d4 decreased the frequency of PDGFRα$^+$ cells and increased the proportion of CXCR4$^+$ cells in all media. See also FIG. 2. Similar results were observed with APEL batches 2 and 3 (data not shown).

APEL Medium is a Robust Platform for Analysing Variables Affecting HESC Differentiation Outcomes Variation in the biological activity of different batches of serum and serum derived components, such as BSA, represents a significant impediment to the translation of differentiation protocols between laboratories. Recombinant human albumin is the main source of protein in APEL medium. All five batches of Albucult® recombinant human albumin (Novozymes Delta Ltd) that have been tested yielded satisfactory differentiation outcomes. Differentiation experiments comparing three preparations of APEL (made with independent lots of Albucult® of similar age) yielded highly consistent results (FIGS. 9-11). This consistency in performance of APEL medium has allowed us to unambiguously identify variations in other components that are critical to differentiation outcomes. As shown in FIG. 1c, MIXL1$^{GFP/w}$ HESCs differentiated in APEL media generate GFP$^+$ cells at a frequency which is dependent on BMP4 concentration. In a similar fashion, PDGFRα$^+$ mesoderm forms in a dose dependent manner in response to BMP4, providing a means to titrate BMP4 activity using any HESC line (FIG. 4). When we compared the induction of PDGFRα expression in spin EBs by two consecutively purchased batches of BMP4, we observed that 30-40 ng/ml of BMP4 batch1 was required to induce the same percentage of PDGFRα$^+$ cells as 10-20 ng/ml of BMP4 batch2, demonstrating a 2-3 fold difference in biological activity. Given the formation of certain cells types, such as cardiac mesoderm (FIGS. 3h, i) can be critically affected by relatively small changes in the concentration of specific factors, the ability to reliably assay the biological activity of these components is likely to be of paramount importance for ensuring experimental reproducibility.

APEL Medium Represents a Stable and Robust Platform for Optimising Conditions for the Directed Differentiation of HESCs.

We speculate that a major contributor to the reproducibility afforded by APEL medium is the absence of animal derived constituents associated with the albumin. However, the relatively high cost of this component prompted us to test a number of other sources of albumin in place of Albucult. Results from differentiation experiments comparing APEL with BPEL (BSA, PVA and Essential Lipids) and HPEL, a medium using a source of clinically certified, purified non-recombinant human albumin, suggested that these media variants could also support the formation of single EBs and efficient mesendodermal differentiation (Tables 2 and 6; FIGS. 9-11). Nevertheless, it is noteworthy that EBs formed in APEL were larger, differentiated more rapidly and yielded a higher number of viable cells than those formed in either BPEL or HPEL. These results demonstrate that impurities associated with albumin components can impinge upon the efficiency of the differentiation process in a detrimental manner.

Demonstration of the Use of AEL Media for HESC Differentiation in Adherent Monolayer Cultures Experiments were conducted to test the ability of AEL (i.e. APEL media without polyvinylalcohol included) to support mesendodermal differentiation of hESCs grown in adherent cultures. hESCs were seeded on fibronectin-coated plates in hESC media (KOSR based formulation). After 5 days the media was changed to AEL supplemented with BMP4 and Activin A. In subsequent experiments, the differentiation medium has been successfully added after 1-2 days. After a further 3-5 days cells were analysed for expression of the stem cell marker, E-CADHERIN and for activation of mesendodermal gene, MIXL1. These were compared to cells that had been maintained in hESC culture media containing FGF2.

Figure 12:
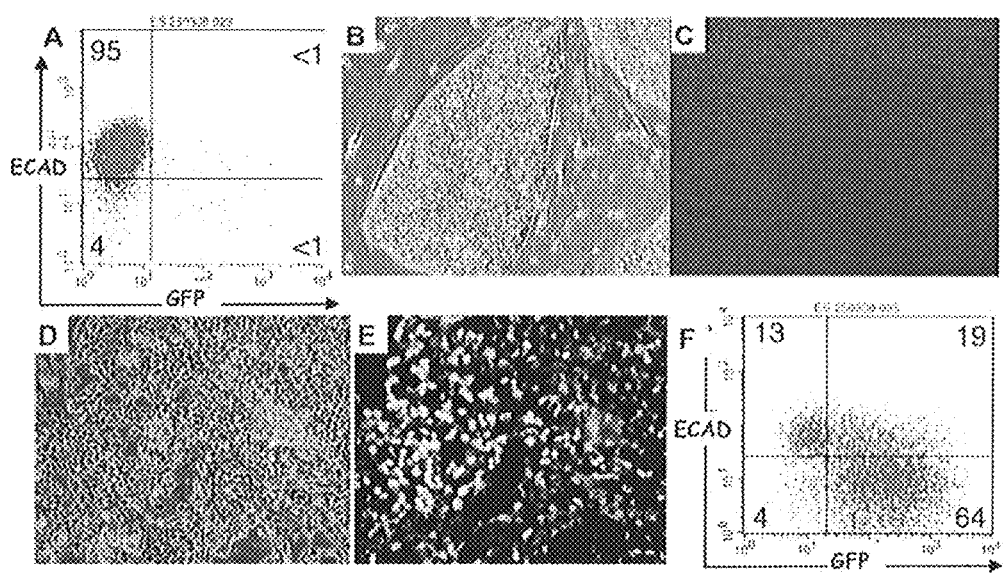
FIG. 12 shows analysis of MIXL1$^{GFP/w}$ hESCs differentiated as flat cultures. A, flow cytometry analysis of control cultures grown in hESC media supplemented with 10 ng/ml FGF2 showing uniform expression of the stem cell marker E-CADHERIN and no expression of GFP from the MIXL1 locus. B, C, Bright field and fluorescent images of cultures grown under these conditions indicates that cells retain an undifferentiated morphology and do not express GFP (MIXL1). D, Bright field image documenting the mesenchymal morphology of cells undergoing mesendoderm formation in response BMP4 and Activin A treatment. E, Fluorescent image of the culture shown in D demonstrating the widespread expression of GFP (MIXL1). F, Flow cytometry analysis of the populations shown in D & E indicating that more that 80% of the cells have differentiated to MIXL1$^+$ mesendoderm. ECAD, E-Cadherin.

MIXL1$^{GFP/w}$ hESCs from control cultures maintained an undifferentiated phenotype whist those cells grown in AEL medium supplemented with BMP4 and Activin A had undergone extensive mesendodermal differentiation. This differentiation was evidenced by the altered morphology of the cells (compare FIG. 12B with FIG. 12D) and activation of GFP expression from the MIXL1 locus in the BMP4/Activin A treated cultures (compare FIG. 12C and FIG. 12E). This conclusion was supported by flow cytometry analysis (compare FIG. 12A and FIG. 12F). Overall, these experiments indicate that AEL medium supports the growth factor dependent differentiation of hESCs toward the mesendoderm. This proof of principle experiment suggests that AEL represents a suitable media for testing or screening for growth factors or small molecules that would promote this differentiation step. Furthermore, it also suggests that this medium would support further differentiation to commitment cells representing the derivatives of both mesoderm and endoderm.

In conclusion, we have developed a medium for the in vitro differentiation of HESCs, denoted APEL, which utilizes only animal and human product free components and recombinant human proteins. The medium requires only commercially available reagents, and it has proved to be robust platform for the differentiation of HESCs in the laboratory. We have not observed variation in the performance of the medium despite using a number of independent batches of components over a 12 month period of testing and we have shown that APEL medium supports multilineage differentiation of spin EBs in all the HESC lines that we have examined. Indeed, the stability of APEL medium has enabled us to identify that variation in the activity of growth factors and sub optimal quality of the undifferentiated HESCs are major causes for poor differentiation outcomes.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed:

1. A serum-free cell differentiation media composition, consisting essentially of: a cell nutrient media; recombinant human albumin; sodium; octanoate; cholesterol; linoleic acid; linolenic acid; and a human embryonic stem cell (HESC) differentiation agent which agent directs the differentiation of the HESC towards a cell lineage selected from the group consisting of ectoderm, mesoderm, endoderm and combinations thereof; and a polymeric alcohol, lactam, an essential fatty acid, a sterol, recombinant human insulin, anti-oxidants, a synthetic form of a naturally occurring amino acid, an antibiotic, transferrin and transferrin substitutes; and a trace element selected from the group consisting of $Ag^+$, $Al^{3+}$, $Ba^{2+}$, $Cd^{2+}$, $Co^{2+}$, $Cr^{3+}$, $Ge^{4+}$, $Se^{4+}$, $Br^-$, $I^-$, $Mn^{2+}$, $F^-$, $Si^{4+}$, $V^{5+}$, $Mo^{6+}$, $Ni^{2+}$, $Rb^+$, $Sn^{2+}$, $Zr^{4+}$ and combinations thereof, wherein the cell nutrient media is free of human and animal products.

2. The serum-free media composition of claim 1, wherein the recombinant human albumin is recombinant alpha-fetoprotein.

3. The serum-free media composition of claim 1, wherein the cell nutrient media is selected from the group consisting of IMDM, F12 and protein free hybridoma medium.

4. The serum-free media composition of claim 1, wherein the polymeric alcohol or lactam is selected from the group consisting of polyvinyl alcohol (PVA), polyethyleneglycol (PEG) and polyvinylpyrrolidone (PVP).

5. The serum-free media composition of claim 1, wherein the synthetic form of the naturally occurring amino acid is selected from the group consisting of L-glutamine, L-asparagine, L-threonine, L-serine, L-cysteine, L-tyrosine, glycine, L-alanine, L-aspartic acid, L-glutamic acid, L-phenylalanine, L-histidine, L-isoleucine, L-lysine, L-leucine, L-methionine, L-proline, L-threonine, L-tryptophan, L-valine and combinations thereof.

6. The serum-free media composition of claim 1, wherein the synthetic form of the naturally occurring amino acid is L-glutamine.

7. The serum-free media composition of claim 1, wherein the anti-oxidant is selected from the group consisting of ascorbic acid, a mercaptol alcohol, glutathione, thiamine, dithiothreitol (DTT) and combinations thereof.

8. The serum-free media composition of claim 7, wherein the anti-oxidant is selected from the group consisting of ascorbic acid, phosphate, and mercaptol alcohol and combinations thereof.

9. The serum-free media composition of claim 7, wherein the mercaptol alcohol is β-mercaptoethanol.

10. The serum-free media composition of claim 1, wherein the antibiotic is selected from the group consisting of penicillin, streptomycin and combinations thereof.

11. The serum-free media composition of claim 1, wherein the transferrin substitute is an iron chelate selected from the group consisting of ferric acid chelate, ferrous sulfate chelate and combinations thereof.

12. The serum-free media composition of claim 1, wherein the trace element is $Se^{4+}$.

13. The serum-free media composition of claim 1, wherein the HESC differentiation agent is selected from one or more growth factors and cytokines.

14. The serum-free media composition of claim 13, wherein the growth factor and cytokine is selected from the group consisting of fibroblast growth factors (FGF), transforming growth factor-β (TFG-β), bone morphogenetic proteins (BMP), vascular endothelial growth factor (VEGF), stem cell factor (SCF), interleukins (IL), Wnt proteins, platelet derived growth factor (PDGF), insulin-like growth factor (IFG), thrombopoietin (TPO), erythropoietin (EPO), retinoic acid (RA) and combinations thereof.

15. The serum-free media composition of claim 14, wherein the fibroblast growth factor (FGF) is FGF-2.

16. The serum-free media composition of claim 14, wherein the transforming growth factor-β (TFG-β) is Activin A.

17. The serum-free media composition of claim 14, wherein the bone morphogenetic protein (BMP) is selected from the group consisting of BMP-2, BMP-4, BMP-5, BMP-7 and combinations thereof.

18. The serum-free media composition of claim 14, wherein the Wnt protein is selected from the group consisting of Wnt3a, Wnt5a and combinations thereof.

19. The serum-free media composition of claim 14, wherein the interleukin is selected from the group consisting of IL-3, IL-6 and combinations thereof.

20. The serum-free media composition of claim 14, wherein the insulin-like growth factor is IGF-2.

21. The serum-free media composition of claim 1, wherein the linoleic acid and linolenic acid are plant derived.

22. A serum-free cell differentiation media composition, consisting essentially of: a cell nutrient media; recombinant human albumin; sodium; octanoate; cholesterol; linoleic acid; linolenic acid; a trace element selected from the group consisting of $Ag^+$, $Al^{3+}$, $Ba^{2+}$, $Cd^{2+}$, $Co^{2+}$, $Cr^{3+}$, $Ge^{4+}$, $Se^{4+}$, $Br^-$, $I^-$, $Mn^{2+}$, $F^-$, $Si^{4+}$, $V^{5+}$, $Mo^{6+}$, $Ni^{2+}$, $Rb^+$, $Sn^{2+}$, $Zr^{4+}$ and combinations thereof; recombinant human insulin, an anti-oxidant; a synthetic form of a naturally occurring amino acid, an antibiotic, transferrin or a transferrin substitute, a compound selected from the group consisting of polyvinyl alcohol (PVA), poly ethyleneglycol (PEG) and polyvinylpyrrolidone (PVP); and a human embryonic stem cell (HESC) differentiation agent which agent directs the differentiation of the HESC towards a cell lineage selected from the group consisting of ectoderm, mesoderm, endoderm and combinations thereof; wherein the cell nutrient media is free of human and animal products.

23. The serum-free media composition of claim 22, wherein the linoleic acid and linolenic acid are plant derived.

24. The serum-free media composition of claim 22, wherein the composition comprises PVA and wherein the trace element is $Se^{4+}$.

25. A serum-tree cell differentiation media composition consisting essentially of: a cell nutrient media; recombinant human albumin; sodium; octanoate; cholesterol; linoleic acid; linolenic acid; a trace element, wherein the trace element is $Se^{4+}$; recombinant human insulin, an anti-oxidant, a synthetic form of a naturally occurring amino acid; an antibiotic, transferrin or a transferrin substitute, polyvinyl alcohol (PVA); and a human embryonic stem cell (HESC) differentiation agent which agent directs the differentiation of the HESC towards a cell lineage selected from the group consisting of ectoderm, mesoderm, endoderm and combinations thereof, wherein the cell nutrient media is free of human and animal products.

26. A serum-free cell differentiation media composition, consisting of: a cell nutrient media; recombinant human albumin; sodium; octanoate; cholesterol; linoleic acid; linolenic acid; and a human embryonic stem cell (HESC) differentiation agent which agent directs the differentiation of the HESC towards a cell lineage selected from the group consisting of ectoderm, mesoderm, endoderm and combinations thereof; and a polymeric alcohol, lactam, an essential fatty acid, a sterol, recombinant human insulin, an anti-oxidants, a synthetic form of a naturally occurring amino acid, an antibiotic, transferrin and transferrin substitutes; and a trace element selected from the group consisting of $Ag^+$, $Al^{3+}$, $Ba^{2+}$, $Cd^{2+}$, $Co^{2+}$, $Cr^{3+}$, $Ge^{4+}$, $Se^{4+}$, $Br^-$, $I^-$, $Mn^{2+}$, $F^-$, $Si^{4+}$, $V^{5+}$, $Mo^{6+}$, $Ni^{2+}$, $Rb^+$, $Sn^{2+}$, $Zr^{4+}$ and combinations thereof, wherein the cell nutrient media is free of human and animal products.

27. A serum-free cell differentiation media composition, consisting of: a cell nutrient media; recombinant human albumin; sodium; octanoate; cholesterol; linoleic acid; linolenic acid; a trace element selected from the group consisting of $Ag^+$, $Al^{3+}$, $Ba^{2+}$, $Cd^{2+}$, $Co^{2+}$, $Cr^{3+}$, $Ge^{4+}$, $Se^{4+}$, $Br^-$, $I^-$, $Mn^{2+}$, $F^-$, $Si^{4+}$, $V^{5+}$, $Mo^{6+}$, $Ni^{2+}$, $Rb^+$, $Sn^{2+}$, $Zr^{4+}$ and combinations thereof; recombinant human insulin, an anti-oxidant, a synthetic form of a naturally occurring amino acid, an antibiotic, transferrin or a transferrin substitute, a compound selected from the group consisting of polyvinyl alcohol (PVA), poly ethyleneglycol (PEG) and polyvinylpyrrolidone (PVP); and a human embryonic stem cell (HESC) differentiation agent which agent directs the differentiation of the HESC towards a cell lineage selected from the group consisting of ectoderm, mesoderm, endoderm and combinations thereof; wherein the cell nutrient media is free of human and animal products.

28. A serum-free cell differentiation media composition consisting of; a cell nutrient media; recombinant human albumin; sodium; octanoate; cholesterol; linoleic acid; linolenic acid; a trace element, wherein the trace element is $Se^{4+}$; recombinant human insulin, an anti-oxidant, a synthetic form of a naturally occurring amino acid, an antibiotic, transferrin or a transferrin substitute, polyvinyl alcohol (PVA); and a human embryonic stem cell (HESC) differentiation agent which agent directs the differentiation of the HESC towards a cell lineage selected from the group consisting of ectoderm, mesoderm, endoderm and combinations thereof; wherein the cell nutrient media is free of human and animal products.

* * * * *

UNITED STATES PATENT AND TRADEMARK OFFICE
CERTIFICATE OF CORRECTION

PATENT NO. : 10,894,944 B2  
APPLICATION NO. : 12/756785  
DATED : January 19, 2021  
INVENTOR(S) : Andrew George Elefanty et al.

Page 1 of 1

It is certified that error appears in the above-identified patent and that said Letters Patent is hereby corrected as shown below:

In the Claims

Column 20, Line 6 In Claim 25, please replace "serum-tree" with --serum-free--.

Signed and Sealed this  
Fifteenth Day of June, 2021

Drew Hirshfeld  
*Performing the Functions and Duties of the*  
*Under Secretary of Commerce for Intellectual Property and*  
*Director of the United States Patent and Trademark Office*